(12) United States Patent
Burkholz et al.

(10) Patent No.: US 12,128,193 B2
(45) Date of Patent: Oct. 29, 2024

(54) EXTENSION SET WITH A PATENCY INSTRUMENT

(71) Applicant: Becton, Dickinson and Company, Franklin Lakes, NJ (US)

(72) Inventors: Jonathan Karl Burkholz, Salt Lake City, UT (US); Megan Scherich, Salt Lake City, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 299 days.

(21) Appl. No.: 17/195,184

(22) Filed: Mar. 8, 2021

(65) Prior Publication Data
US 2021/0290906 A1 Sep. 23, 2021

Related U.S. Application Data

(60) Provisional application No. 62/993,674, filed on Mar. 23, 2020.

(51) Int. Cl.
*A61M 25/01* (2006.01)
*A61M 25/09* (2006.01)
*A61M 39/14* (2006.01)

(52) U.S. Cl.
CPC .... *A61M 25/0122* (2013.01); *A61M 25/0136* (2013.01); *A61M 25/09* (2013.01); *A61M 39/14* (2013.01)

(58) Field of Classification Search
CPC ........... A61M 2025/0019; A61M 2025/09116; A61M 2025/0912; A61M 25/0017;

(Continued)

(56) References Cited

U.S. PATENT DOCUMENTS 2,799,273 A * 7/1957 Oddo ................. A61M 25/1011
604/101.05
3,583,404 A * 6/1971 McWhorter ........ A61M 27/008
604/266

(Continued)

FOREIGN PATENT DOCUMENTS

WO 2016100868 A1 6/2016

OTHER PUBLICATIONS

Scherich, et al., Flush Instrument with Blood Exposure Protection and Related Methods, U.S. Appl. No. 17/127,588, filed Dec. 18, 2020.

(Continued)

*Primary Examiner* — Jason E Flick
*Assistant Examiner* — Adam J. Cermak
(74) *Attorney, Agent, or Firm* — The Webb Law Firm (57) ABSTRACT

An extension set may include a tube, which may include a distal end, a proximal end, and an outer surface. The extension set may include a distal connector coupled to the distal end of the tube and/or a proximal connector coupled to the proximal end of the tube. The extension set may include a patency instrument disposed within the tube. The extension set may include a translation handle coupled to the outer surface of the tube. The translation handle may be configured to move along the outer surface of the tube between a proximal position and a distal position to translate the distal end of the patency instrument between a retracted position and an advanced position. In response to the distal end of the patency instrument being in the advanced position, the distal end of the patency instrument may extend beyond the distal end of the tube.

13 Claims, 5 Drawing Sheets

(58) Field of Classification Search
CPC .......... A61M 25/0905; A61M 25/0111; A61M 25/0113; A61M 2005/1583; A61M 2005/1585; A61M 2210/1096
See application file for complete search history.

(56) References Cited

U.S. PATENT DOCUMENTS

| | | | | |
|---|---|---|---|---|
| 3,766,915 A * | 10/1973 | Rychlik | ............ | A61M 25/0631 604/161 |
| 4,889,106 A * | 12/1989 | Watanabe | ............... | A61B 10/04 600/101 |
| 5,059,186 A * | 10/1991 | Yamamoto | ......... | A61M 25/0111 604/167.03 |
| 5,397,310 A * | 3/1995 | Chu | .................. | A61M 39/0613 604/167.03 |
| 5,505,714 A * | 4/1996 | Dassa | .................. | A61M 39/12 604/534 |
| 5,598,840 A * | 2/1997 | Iund | .................. | A61M 16/0463 128/207.14 |
| 6,183,450 B1 * | 2/2001 | Lois | ...................... | A61M 25/00 604/164.01 |
| 6,585,703 B1 * | 7/2003 | Kassel | ............... | A61M 25/0668 604/263 |
| 6,712,790 B1 * | 3/2004 | Prestidge | ........... | A61B 5/15003 604/177 |
| 7,699,809 B2 * | 4/2010 | Urmey | .............. | A61M 25/0606 607/116 |
| 9,744,344 B1 * | 8/2017 | Devgon | ........... | A61M 39/0247 |
| 10,226,594 B1 * | 3/2019 | Palmer | .................. | A61M 27/00 |
| 11,207,498 B2 * | 12/2021 | Devgon | ............ | A61M 39/0247 |
| 2005/0143625 A1 * | 6/2005 | Whitmore | .......... | A61B 1/00142 600/171 |
| 2006/0025753 A1 * | 2/2006 | Kubalak | ............ | A61M 25/0111 604/327 |
| 2008/0159825 A1 * | 7/2008 | Tegg | ................. | A61M 25/0133 411/262 |
| 2008/0319387 A1 * | 12/2008 | Amisar | ............ | A61M 25/0606 604/533 |
| 2009/0076417 A1 * | 3/2009 | Jones | .............. | A61M 25/09041 600/585 |
| 2009/0137986 A1 * | 5/2009 | Golden | ................ | A61M 25/013 220/735 |
| 2009/0188531 A1 * | 7/2009 | Boyle, Jr. | ................ | A61M 1/87 134/146 |
| 2009/0306591 A1 * | 12/2009 | Amisar | .................. | A61M 25/01 604/122 |
| 2010/0210934 A1 * | 8/2010 | Belson | ............. | A61B 5/150503 600/371 |
| 2010/0312227 A1 * | 12/2010 | House | ............... | A61M 25/0017 604/544 |
| 2011/0077621 A1 * | 3/2011 | Graham | ............. | A61M 39/1011 604/528 |
| 2013/0028546 A1 * | 1/2013 | Wako | ...................... | F16C 33/36 384/49 |
| 2013/0096505 A1 * | 4/2013 | Urmey | ............... | A61M 25/0113 604/165.01 |
| 2013/0110087 A1 * | 5/2013 | Kane | ..................... | A61M 27/00 15/104.03 |
| 2016/0030984 A1 * | 2/2016 | Rife | ...................... | A61B 90/70 134/8 |
| 2016/0175560 A1 | 6/2016 | Tallarida et al. | | |
| 2016/0213883 A1 * | 7/2016 | Schwarz | ............ | A61M 25/0113 |
| 2016/0213889 A1 * | 7/2016 | Sos | ........................ | B65B 63/04 |
| 2016/0339205 A1 * | 11/2016 | Foley | ................... | A61M 27/00 |
| 2017/0042571 A1 * | 2/2017 | Levi | ...................... | A61F 2/2427 |
| 2017/0216564 A1 * | 8/2017 | Devgon | ........... | A61B 5/150259 |
| 2017/0291010 A1 * | 10/2017 | Bonneau | ............... | A61M 39/10 |
| 2019/0021640 A1 | 1/2019 | Burkholz et al. | | |
| 2019/0046767 A1 * | 2/2019 | Palmer | ................ | A61M 25/002 |
| 2019/0321590 A1 | 10/2019 | Burkholz et al. | | |
| 2021/0001086 A1 * | 1/2021 | Berul | ................ | A61M 25/0113 |
| 2021/0228837 A1 * | 7/2021 | Palmer | .................... | A61M 1/69 |

OTHER PUBLICATIONS

Burkholz, et al., Multi-lumen Extension System, U.S. Appl. No. 17/127,623, filed Dec. 18, 2020.

* cited by examiner

EXTENSION SET WITH A PATENCY INSTRUMENT

RELATED APPLICATIONS

This application claims the benefit of U.S. Provisional Patent Application No. 62/993,674, filed on Mar. 23, 2020, entitled "EXTENSION SET WITH A PATENCY INSTRUMENT," which is incorporated herein in its entirety.

BACKGROUND

Patency is the state or quality of a fluid channel within a patient's body being free of blockages. Specifically, an intravenous (IV) device may have a level of patency when a fluid such as blood or a medicament may pass through the IV device. During use of an IV device, the IV device is inserted into a patient's blood vessel and, in some embodiments, a needle is pulled out of a catheter while the catheter remains within the patient's blood vessel. In some circumstances, the IV device is left to remain in the patient's blood vessel for up to 30 or more days. This is done so as to allow a clinician or other health care provider (HCP) to have fluidic access to the patient's blood stream during care. This continuous fluid access to the patient's blood stream allows a clinician or other HCP to, when appropriate, draw one or a plurality of blood samples or administer one or more infusing fluids, such as normal saline solution, various medicaments, and total parenteral nutrition.

The patency of the IV device may be compromised, however, while the IV device is within the patient's blood vessel. Any blockage may persist and cause the IV device to fail necessitating another administration of an IV device into the patient's body. This may increase the trauma felt by the patient and lead to other medical issues such as inflammation of the blood vessel among other medical issues.

The subject matter claimed herein is not limited to embodiments that solve any disadvantages or that operate only in environments such as those described above. Rather, this background is only provided to illustrate one example technology area where some implementations described herein may be practiced.

BRIEF SUMMARY

The present disclosure relates generally to an extension set used to interface with an IV device that provides for a fluidic path to the IV device while also providing for a patency instrument used to periodically check or improve the patency of the IV device while the IV device is within a patient's blood vessel. In some embodiments, an extension set may include a tube, which may include a distal end, a proximal end, a lumen extending between the distal end and the proximal end, and an outer surface. In some embodiments, the tube may include or correspond to any suitable housing that includes a lumen extending therethrough.

In some embodiments, the extension set may include a distal connector coupled to the distal end of the tube. In some embodiments, the extension set may include a proximal connector coupled to the proximal end of the tube. In some embodiments, the extension set may include a patency instrument disposed within the tube. In some embodiments, the patency instrument may include a guidewire or another suitable patency enhancing structure.

In some embodiments, the extension set may include a translation handle coupled to the outer surface of the tube. In some embodiments, the translation handle may be configured to move along the outer surface of the tube between a proximal position and a distal position to translate the distal end of the patency instrument between a retracted position and an advanced position. In some embodiments, in response to the distal end of the patency instrument being in the advanced position, the distal end of the patency instrument may extend beyond the distal end of the tube.

In some embodiments, the extension set may include a coupler element disposed within the tube. In some embodiments, the patency instrument may extend distally from the coupler element. In some embodiments, the translation handle may compress a portion of the tube in between the coupler element and the translation handle. In some embodiments, the portion of the tube may engage the coupler element such that movement of the translation handle along the outer surface of the tube translates the coupler element within the tube and the distal end of the patency instrument is moved between the retracted position and the advanced position. In some embodiments, the translation handle may include multiple ball bearings or multiple wheels to provide localized compression of the tube to engage the coupler element.

In some embodiments, the extension set may include another tube. In some embodiments, the other tube may include or correspond to any suitable housing that includes a lumen extending therethrough. In some embodiments, the other tube may be disposed within the tube and extend through the coupler element. In some embodiments, a space between the other tube and the tube is sealed such that fluid is prevented from entering the space. In some embodiments, the other tube may form a fluidic channel, while the space may correspond to a non-fluidic channel. In some embodiments, the patency instrument may extend through the space.

In some embodiments, the extension set may include a seal adjacent the distal end of the tube. In some embodiments, the seal may be disposed within the distal connector and/or within the distal end of the tube. In some embodiments, the other tubing and the patency instrument may extend through the seal. In some embodiments, a distal end of the space may be sealed by the seal such that fluid is prevented from entering the space.

In some embodiments, the extension set may include one or more fluid paths disposed within a wall of the tube. In some embodiments, the lumen may be sealed from the fluid paths, which may correspond to fluidic channels, and the patency instrument may extend through the lumen, which may correspond to a non-fluidic channel. In some embodiments, the fluid paths may form protrusions into the lumen of the tube. In some embodiments, an outer surface of the coupler element may include one or more grooves aligned with the protrusions. In some embodiments, the grooves may extend through the coupler element. In some embodiments, the seal may include holes aligned with the fluid paths, and may seal the lumen from the fluid paths.

In some embodiments, a method to provide access to a patient's vascular system may include coupling the extension set to a catheter assembly or another IV device. In some embodiments, coupling the extension set to the catheter assembly may include coupling the distal end of the tube to the catheter assembly. In some embodiments, the method may include moving the translation handle along the tube from the proximal position to the distal position. In some embodiments, in response to the translation handle moving to the distal position, the distal end of the patency instrument may extend beyond the distal end of the tube into the catheter assembly and/or vasculature of the patient. In these embodiments, the patency instrument may extend beyond a distal end of a catheter of the catheter assembly.

In some embodiments, the method may include coupling a blood collection device to the proximal connector after moving the translation handle along the tube from the proximal position to the distal position. In some embodiments, the method may include after collecting blood within the blood collection device, moving the translation handle from the distal position to the proximal position. In some embodiments, in response to moving the translation handle from the distal position to the proximal position, the distal end of the patency instrument may be retracted into the tube.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION

As used herein, the terms "proximal" and "distal" may refer to the direction closer to and away from, respectively, a clinician who would place the catheter system into contact with a patient. Thus, for example, the end of the catheter system first touching the body of the patient would be the distal end, while the opposite end of the catheter system would be the proximal end of the catheter system.

Figure 1A:
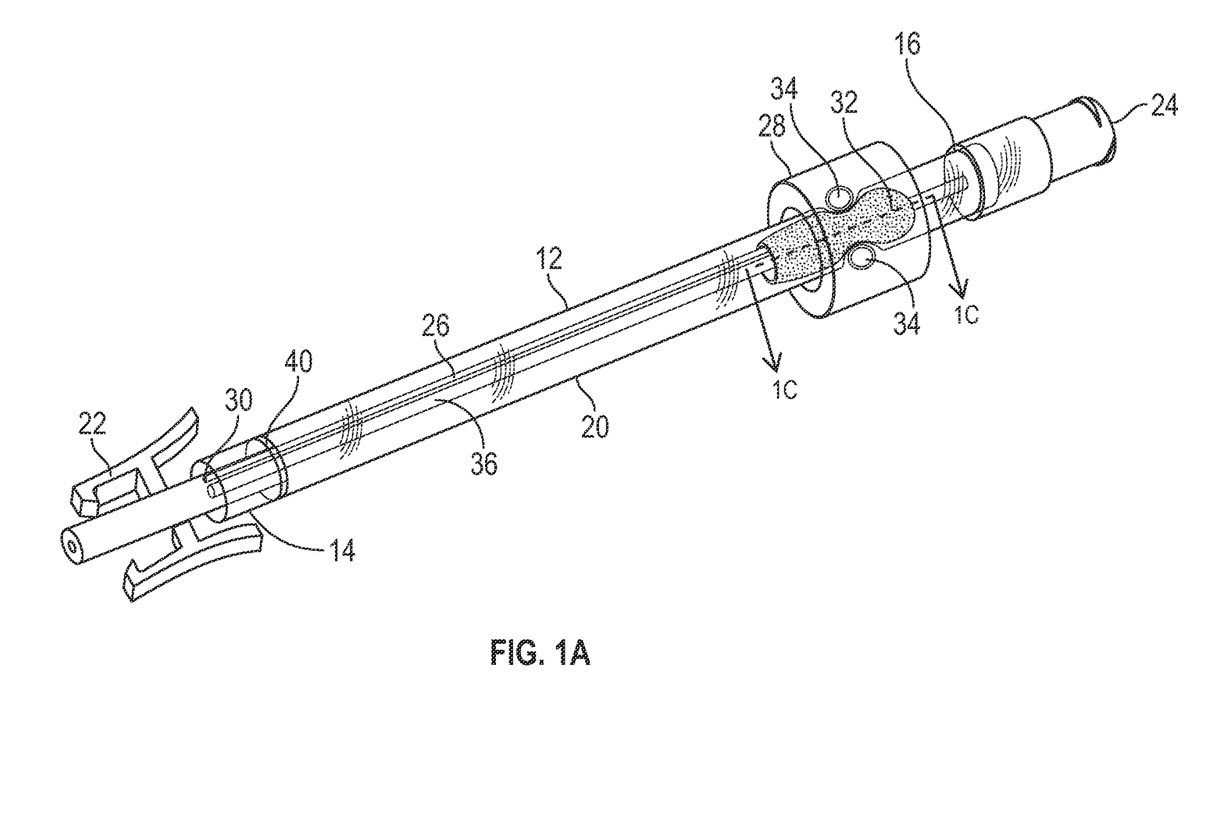
FIG. 1A is an upper perspective view of an example extension set, illustrating an example patency instrument in a retracted position, according to some embodiments.
Figure 1B:
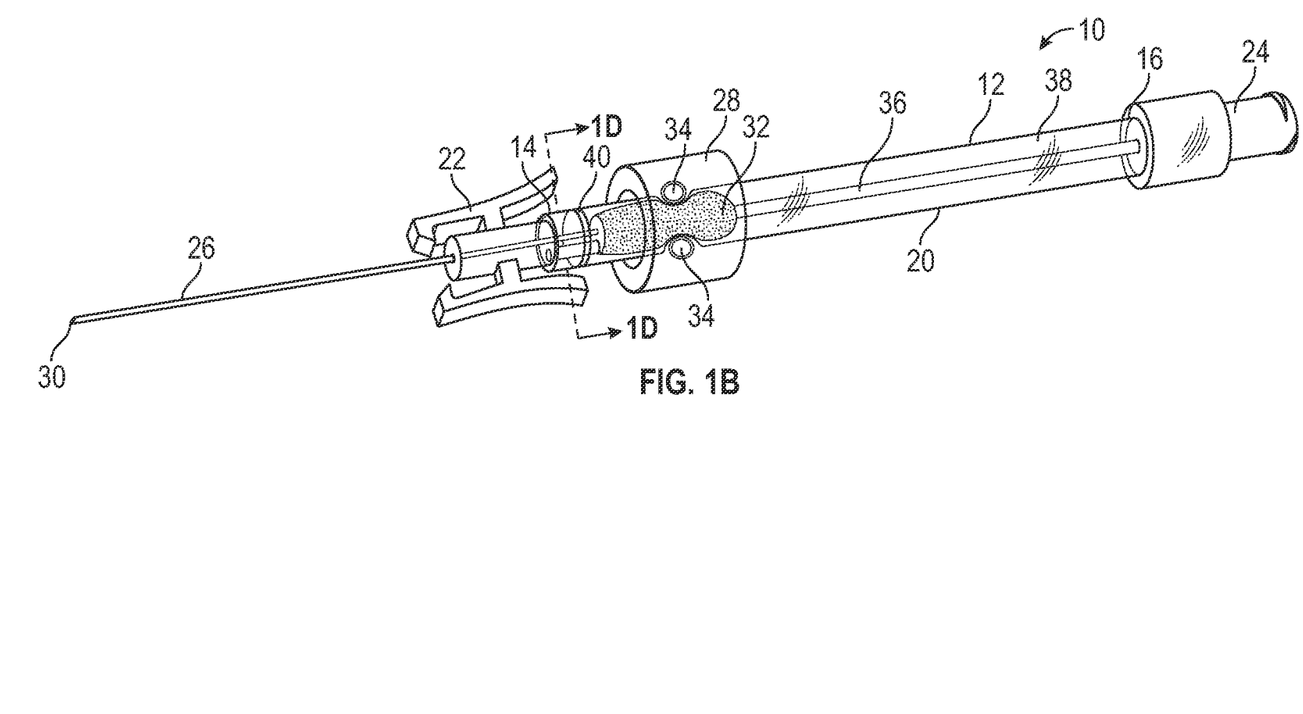
FIG. 1B is an upper perspective view of the extension set of FIG. 1A, illustrating the patency instrument in an advanced position, according to some embodiments.
Figure 1C:
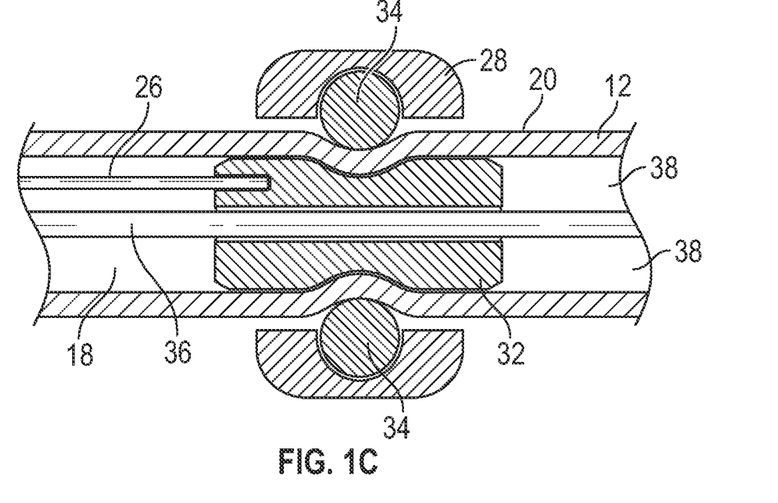
FIG. 1C is a cross-sectional view of a portion of the extension set of FIG. 1A, according to some embodiments.

Referring now to FIGS. 1A-1C, in some embodiments, an extension set 10 may include a tube 12, which may include a distal end 14, a proximal end 16, a lumen 18 extending between the distal end 14 and the proximal end 16, and an outer surface 20. In some embodiments, the tube 12 may include or correspond to any suitable housing that includes a lumen extending therethrough.

In some embodiments, the extension set 10 may include a distal connector 22 coupled to the distal end 14 of the tube 12. In some embodiments, the distal connector 22 may include a male luer connector, a female luer connector, a blunt cannula and opposing lever arms (as illustrated, for example in FIGS. 1A-1B), or another suitable connector configured to couple to a catheter assembly or another IV device. In some embodiments, the extension set 10 may include a proximal connector 24 coupled to the proximal end 16 of the tube 12. In some embodiments, the proximal connector 24 may include a male luer connector, a female luer connector, a needleless access connector, a blunt cannula and opposing lever arms (as illustrated, for example in FIGS. 1A-1B), or another suitable connector. In some embodiments, the proximal connector 24 may include a luer and/or may be coupled to a needleless access connector, such as via threading, bonding, or another suitable method.

In some embodiments, the extension set 10 may include a patency instrument 26 disposed within the tube 12. In some embodiments, the patency instrument 26 may include a guidewire or another suitable patency enhancing structure. In some embodiments, the guidewire may be generally constructed as a wire, a spring, a combination of a wire and a spring, and/or the like. In some embodiments, the extension set 10 may include a translation handle 28 coupled to the outer surface 20 of the tube 12.

In some embodiments, the translation handle 28 may include any suitable translation handle or grip and the patency instrument 26 may include any suitable patency instrument. The translation handle 28 and/or the patency instrument 26 may be described, for example, in further detail in U.S. patent application Ser. No. 17/127,588, filed Dec. 18, 2020, entitled "FLUSH PATENCY INSTRUMENT WITH BLOOD EXPOSURE PROTECTION AND RELATED METHODS" and U.S. patent application Ser. No. 17/127,623, filed Dec. 18, 2020, entitled "MULTI-LUMEN EXTENSION SYSTEM," which are incorporated by reference in their entirety.

In some embodiments, the translation handle 28 may be configured to move along the outer surface 20 of the tube 12 between a proximal position and a distal position to translate a distal end 30 of the patency instrument 26 between a retracted position and an advanced position. In some embodiments, in response to the distal end 30 of the patency instrument 26 being in the advanced position, the distal end 30 of the patency instrument 26 may extend beyond the distal end 14 of the tube 12 and the distal connector 22.

In some embodiments, the patency instrument 26 extends from a coupler element 32 disposed within the tube 12. In some embodiments, a proximal end of the patency instrument 26 may be secured within the coupler element 32. In some embodiments, the patency instrument 26 may extend distally from the coupler element 32. In some embodiments, the patency instrument 26 may extend distally from the coupler element 32 to facilitate translating the patency instrument 26 within the tube 12 without requiring direct contact.

In some embodiments, the translation handle 28 may compress a portion of the tube 12 in between the coupler element 32 and the translation handle 28. In some embodiments, the portion of the tube 12 may engage the coupler element 32 such that movement of the translation handle 28 along the outer surface 20 of the tube 12 translates the coupler element 32 within the tube 12 and the distal end 30 of the patency instrument 26 is moved between the retracted position and the advanced position. In some embodiments, the translation handle 28 may include multiple features 34, which may include ball bearings, wheels, low-friction sliders, or other suitable features to provide localized compression of the tube to engage the coupler element. In some embodiments, the features 34 may be coupled to the translation handle 28. In some embodiments, the features 34 may be directly coupled to the translation handle 28. In some embodiments, the features 34 and the translation handle 28 may be molded together or monolithically formed as a single unit. In some embodiments, the features 34 and the translation handle 28 may be integrated or fitted together.

In some embodiments, the features 34 may include a pinch mechanism and may be positioned to pinch or press against the outer surface of the tube 12. In some embodiments, one or more of the features 34 may oppose or be on opposite sides of the tube 12 as one or more other of the features 34. In some embodiments, an interior surface of the tube 12 within the translation handle 28 may be too small to permit passage of the coupler element 32 therethrough. In some embodiments, the features 34 may include wheels, which may be rotatably coupled to the translation handle 28. In some embodiments, the features 34 may include the ball bearings, which may be rotatable within sockets formed in the translation handle 28. In some embodiments, the features 34 may include sliders, which may be slick and/or constructed of plastic, and which may slide along the tube 12. In some embodiments, the sliders may be stationary or static with respect to the translation handle.

In some embodiments, the translation handle 28 may extend partially (e.g. a c-channel) or entirely around the tube 12. In some embodiments, the translation handle 28 may include a collar. In some embodiments, the coupler element 32 may be magnetically attracted to the translation handle 28 through the tube 12 to facilitate movement of the patency instrument 26 without direct contact.

In some embodiments, the extension set 10 may include another tube 36. In some embodiments, the other tube 36 may include or correspond to any suitable housing that includes a lumen extending therethrough. In some embodiments, the other tube 36 may be disposed within the tube 12 and may extend through the coupler element 32. In some embodiments, a space 38 between the other tube 36 and the tube 12 may be sealed such that fluid is prevented from entering the space 38. In some embodiments, the other tube 36 may form a fluidic channel, while the space 38 may correspond to a non-fluidic channel. In some embodiments, the patency instrument 26 may extend through the space 38. In some embodiments, the space 38 may be part of the lumen 18 and/or annular.

In some embodiments, the extension set 10 may include a seal 40 adjacent the distal end 14 of the tube 12. In some embodiments, the seal 40 may be elastomeric. In some embodiments, the seal 40 may be disposed within the distal connector 22 and/or within the distal end 14 of the tube 12. In some embodiments, a distal end of the space 38 may be sealed by the seal 40 such that fluid is prevented from entering the space 38.

In some embodiments, the lumen 18, such as the space 38, may include venting to allow airflow into and out of the lumen 18, which may facilitate movement of the translation handle 28 and coupler element 32. In some embodiments, one or more vents to provide the venting may be reduced in size to allow air movement while still maintaining good aseptic protection of the patency instrument 26 and/or other portions of the extension set 10.

In some embodiments, the patency instrument 26 may be centered within the tube 12, which may facilitate smooth advancement of the patency instrument 26. In these and other embodiments, the other tube 36 may be off-center within the tube 12. In some embodiments, as the patency instrument 26 may be off-center within the tube 12 and/or the other tube 36 may be centered within the tube 12.

In some embodiments, an outer surface of the coupler element 32 and/or an inner surface of the tube 12 may include a lubricant to facilitate translation of the patency instrument 26 within the tube 12. In some embodiments, an outer surface of the tube 12 and/or the features 34 may include the lubricant. In some embodiments, one or more of the following: the coupler element 32, the tube 12, and the features 34, may be constructed from a lubricious material, such as, for example, PEG polyurethane, siliconized polyurethane, fluorinated polyurethane, silicone, or another suitable material to reduce friction.

In some embodiments, the tube 12 may be flexible. In some embodiments, the outer surface 20 of the tube 12 may include one or more visual markings or tactile elements (detents, grooves, ribs, or the like) to provide user feedback regarding a position of the patency instrument 26 with respect to the IV device. In some embodiments, an inner surface of the coupler element 32 and/or an outer surface of the other tube 36 may include the lubricant, which may facilitate movement of the coupler element 32 with respect to the other tube 36, which may be stationary. In some embodiments, a distal end and/or a proximal end of the other tube 36 may be secured within the extension set 10. In some embodiments, the proximal end of the other tube 36 may be wedged or secured within the proximal connector 24 such that blood cannot flow between the proximal connector 24 and the other tube 36 into the space 8.

Figure 1D:
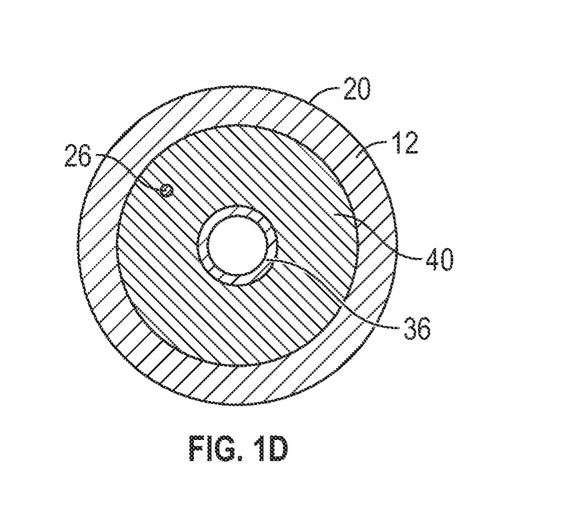
FIG. 1D is a cross-sectional view of the extension set of FIG. 1B along the line 1D-1D of FIG. 1B, according to some embodiments.

Referring now to FIG. 1D, in some embodiments, the other tube 36 and the patency instrument 26 may extend through the seal 40, which may contact edges of the other tube 36 and the patency instrument 26 such that fluid is prevented from flowing between the seal 40 and the other tube 36 and between the seal 40 and the patency instrument 26. In some embodiments, the distal end 30 of the patency instrument 26 may be proximal to the seal 40 in response to the translation handle 28 being in the proximal position, which may include a fully retracted position. In these and other embodiments, the patency instrument 26 extend through the seal 40 in response to movement of the translation handle 28 from the proximal position to the distal position.

Figure 2A:
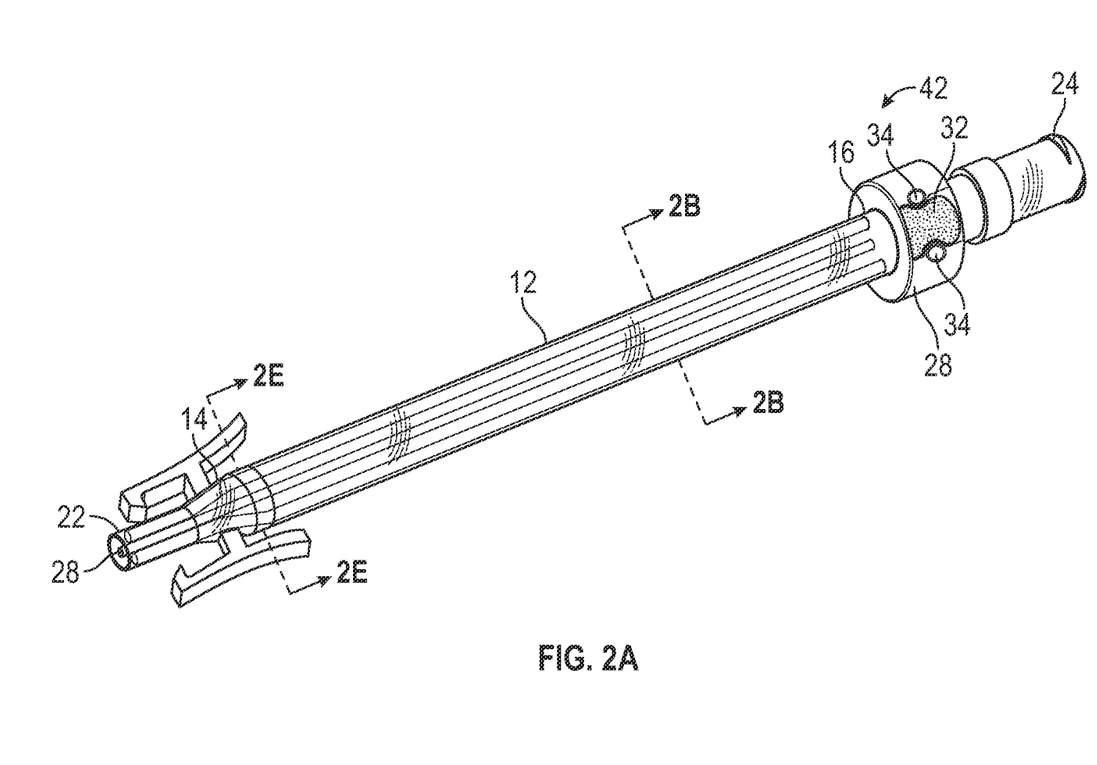
FIG. 2A is an upper perspective view of another example extension set, illustrating an example patency instrument in a retracted position, according to some embodiments.
Figure 2B:
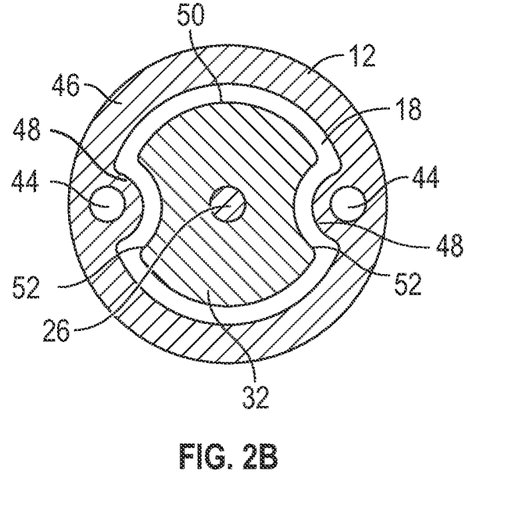
FIG. 2B is a cross-sectional view of the extension set of FIG. 2A along the line 2B-2B, according to some embodiments.

Referring now to FIGS. 2A-2B, an extension set 42 is illustrated, according to some embodiments. In some embodiments, the extension set 42 may be similar or identical to the extension set 10 in terms of one or more features and/or operation. In some embodiments, the extension set 42 may include one or more fluid paths 44 disposed within a wall 46 of the tube 12. In some embodiments, the lumen 18 may be sealed from the fluid paths 44, which may correspond to fluidic channels, and the patency instrument 26 may extend through the lumen 18, which may correspond to a non-fluidic channel. In some embodiments, the fluid paths 44 may be arranged in various positions and configurations within the wall 46.

Figure 2C:
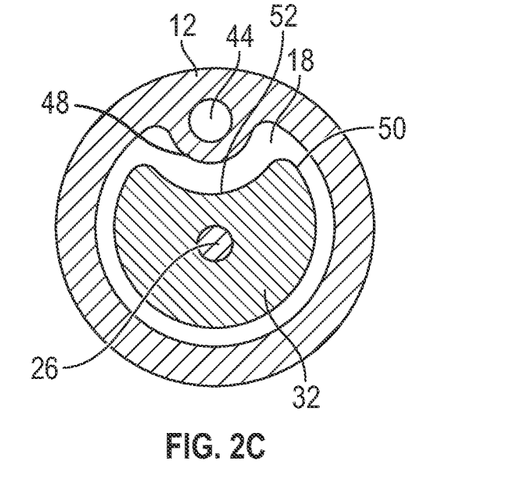
FIG. 2C is an alternative cross-sectional view of the extension set of FIG. 2A along the line 2B-2B, according to some embodiments.
Figure 2D:
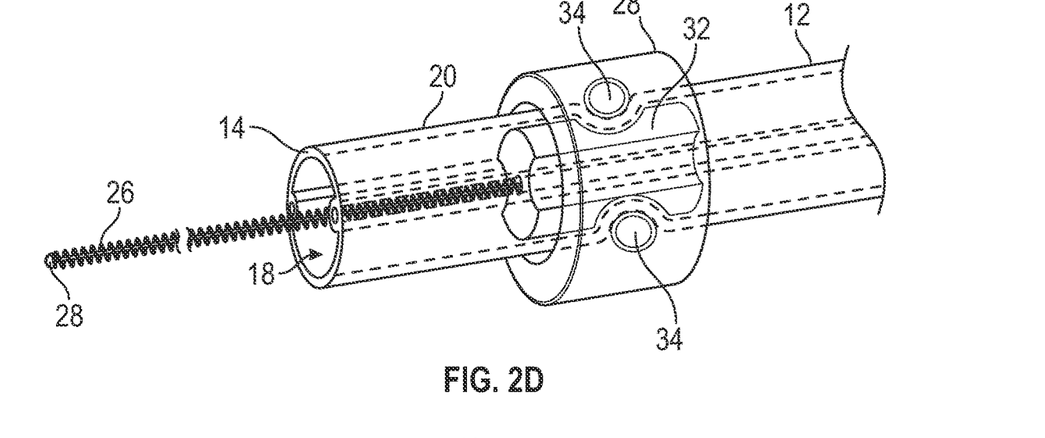
FIG. 2D is an upper perspective view of the extension set of FIG. 2A, illustrating another example patency instrument in an advanced position, and an example distal connector removed for illustrative purposes, according to some embodiments.

Referring now to FIGS. 2B-2D, in some embodiments, the fluid paths 44 may form protrusions 48 into the lumen 18 of the tube 12 and a thickness of the wall 46 may vary. In some embodiments, the fluid paths 44 may protrude inwardly from the wall 46 towards a central axis of the tube 12, for example, or outwardly from the wall 46 and away from the central axis of the tube 12. In some embodiments, an outer surface 50 of the coupler element 32 may include one or more grooves 52 aligned with the protrusions 48. In some embodiments, the grooves 52 may extend through the coupler element 32 and may facilitate movement and/or guidance of the coupler element 32 within the tube 12. In some embodiments, a thinner portion of the wall 46 may reduce a force needed to translate the patency instrument 26.

In some embodiments, the tube 12 may be extruded via a co-extrusion process that includes a first material and a second material harder than the first material. In some embodiments, the first material may form a portion of the tube 12 that is pinched by features 34, and the second material may form another portion of the tube 12 proximate and/or forming the fluid paths 44. In some embodiments, the first material and the portion of the tube 12 may be soft or flexible. In some embodiments, the fluid paths 44 may be created by a multi-lumen extrusion process or may be created as a separate extruded tube that is encompassed within an inner diameter of the tube 12 of the larger non-fluid path extension tubing. In some embodiments, the separate extruded tube may be concentrically aligned or offset from the axis of the tube 12. Alternatively, in some embodiments, the fluid paths 44 could extend from another component of the extension set 42, such as a particular connector or cannula. In some embodiments, a volume of the lumen 18 may be greater than a volume of each of the fluid paths 44, which may accommodate the coupler element 32.

Figure 2E:
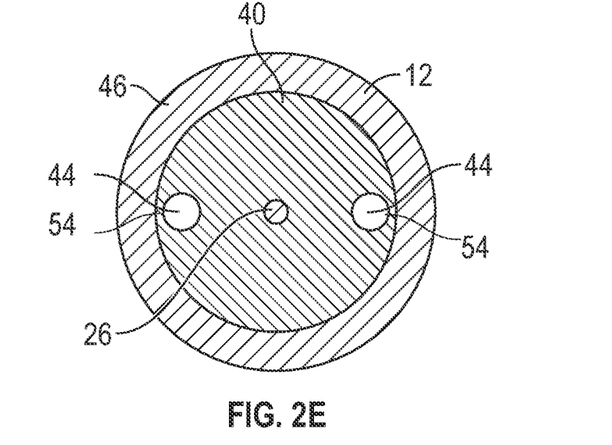
FIG. 2E is a cross-sectional view of the extension set of FIG. 2A along the line 2E-2E, according to some embodiments.

Referring now to FIG. 2E, in some embodiments, the seal 40 may include holes 54 aligned with the fluid paths 44, and may seal the lumen 18 from the fluid paths 44. In some embodiments, the seal 40 may contact an edge of the patency instrument 26 such that fluid is prevented from flowing between the seal 40 and the patency instrument 26.

In some embodiments, a method to provide access to a patient's vascular system may include coupling an extension set (such as, for example, the extension set 10 discussed with respect to FIGS. 1A-1D or the extension set 42 discussed with respect to FIGS. 2A-2E) to a catheter assembly or another IV device. In some embodiments, the catheter assembly may be dwelling within the vasculature of the patient when the extension set is coupled to the catheter assembly, and the patency instrument 26 may increase patency of the catheter assembly throughout dwell time.

In some embodiments, coupling the extension set to the catheter assembly may include coupling the distal end 14 of the tube 12 to the catheter assembly. In some embodiments, the method may include moving the translation handle 28 along the tube 12 from the proximal position to the distal position. In some embodiments, in response to the translation handle 28 moving to the distal position, the distal end 30 of the patency instrument 26 may extend beyond the distal end 14 of the tube 12 into the catheter assembly and/or vasculature of the patient. In these embodiments, the patency instrument 26 may extend beyond a distal end of a catheter of the catheter assembly. In some embodiments, the catheter may include a peripheral IV catheter, a peripherally-inserted central catheter, or a midline catheter.

In some embodiments, the method may include coupling a blood collection device to the proximal connector 24 after moving the translation handle 28 along the tube 12 from the proximal position to the distal position. In some embodiments, the blood collection device may include any suitable blood collection device, such as, for example, a VACUTAINER© or a VACUTAINER© LUER-LOK™, available from Becton Dickinson and Company of Franklin Lakes, New Jersey, a syringe, or a point of care acquisition device. In some embodiments, the blood collection device may be integrated with or monolithically formed as a single unit with the proximal connector 24.

In some embodiments, the method may include after collecting blood within the blood collection device, moving the translation handle 28 from the distal position to the proximal position. In some embodiments, in response to moving the translation handle 28 from the distal position to the proximal position, the distal end 30 of the patency instrument 26 may be retracted into the tube.

In some embodiments, the extension set may reduce hemolysis of a blood sample collected via the fluid path, which may include the other tube 36 (discussed for example, with respect to FIGS. 1A-1D) or the fluid paths 44. In some embodiments, the extension set may provide an adequate fluid flow rate. Blood cell experiences shear stress as it flows in a fluid pathway. The maximum shear stress is along the wall of the blood cell, or wall shear stress. Wall shear stress on blood cells is considered a major source of mechanical damage to blood cells. For a cylindrical fluid path, the wall shear stress is typically expressed as:

$$T = \frac{1}{2} \cdot \frac{\Delta p}{L} \cdot (kr)$$

in which ΔP is the pressure drop along a path with a length of L and an interior radius of r. k is shrinkage index.

To fill a certain volume of collection tube, V, with a flow rate of Q, the time needed can be simply assessed by:

$$t = \frac{v}{Q} = 8\mu v \cdot \frac{1}{\pi r^4} / \left(\frac{\Delta p}{L}\right)$$

in which μ is the dynamic viscosity of the fluid. Hemolysis is typically associated with both the wall shear stress and the time a blood cell is exposed to wall shear stress. From literature, it has been widely considered that hemolysis index can be approached as a function of:

$$HI(\%) = A * t^\alpha * T^\beta$$

in which A, α, and β are coefficients.

In principle, the hemolysis index is related to pressure gradient and cross-sectional characteristic dimension:

$$HI(\%) \propto \left(\frac{\Delta P}{l}\right)^{\beta-\alpha} \cdot \left(\frac{1}{r}\right)^{4\alpha-\beta}$$

In some embodiments, a length of the other tube 36 and/or the fluid paths 44 may be selected based on one or more of the following: a gauge of a particular catheter, a particular catheter assembly configuration, or a clinical setup. In some embodiments, the patency instrument 110 may include a length L. In some embodiments, the other tube 36 and/or the fluid paths 44 may include an inner diameter D.

Fluid flow in a fluid pathway (such as the that of the other tube 36 and/or the fluid paths 44) can be analyzed using Poiseuille's equation when the fluid pathway is tubular:

$$Q = \frac{\pi D^4 \Delta P}{128 \mu L} = \frac{\Delta P}{R_f}$$

where $\Delta P$ is a change in pressure gradient across the length of the fluid pathway, D and L are the inner diameter and length, respectively, of the fluid pathway, $\mu$ is the viscosity of a fluid, and $$R_f = \frac{128 \mu L}{\pi D^4}$$

is the fluid resistance. Since $\mu$ is the viscosity of the fluid and not part of the extension tube geometry, a geometric factor $G_f$ is defined such that $R_f$ (the fluid resistance) is $$R_f = \frac{128 \mu}{\pi} G_f,$$

where $$G_f = \frac{L}{D^4}.$$

In some embodiments, the fluid pathway may have multiple sections with lengths (L1, L2, L3) and inner diameters of (D1, D2, D3), the geometric factor is then:

$$G_f = \frac{L1}{D1^4} + \frac{L2}{D2^4} + \frac{L3}{D3^4}$$

In some embodiments, the fluid pathway may have an inner diameter that changes over the length of the fluid pathway, the geometric factor is then:

$$G_f = \int_0^L \frac{dl}{D(l)^4}$$

In some embodiments, the fluid pathway may have a cross section that is not circular or may have a complicated inner diameter profile. The geometric factor can then be determined by measuring the flow rate (Q) at given pressure ($\Delta P$) with known viscosity ($\mu$) fluid:

$$G_f = \frac{\pi \Delta P}{128 \mu Q}$$

The $G_f$ value of the fluid pathway may be selected to reduce the maximum shear stress for each catheter gauge to be the same or less than the max shear stress of a BD 21G VACUTAINER® UltraTouch™ push button blood collection set (available from Becton, Dickinson & Company of Franklin Lakes, New Jersey), which was previously considered the gold standard for blood draws. In some embodiments, $G_f$ value of the fluid pathway may be selected to reduce the maximum shear stress for each catheter gauge to be the same or less than the max shear stress of a BD 25G VACUTAINER® UltraTouch™ push button blood collection set (available from Becton, Dickinson & Company of Franklin Lakes, New Jersey).

In some embodiments, an extended fluid pathway of a blood collection system, which may include one or more of the blood collection device, the other tube 36 and/or the fluid paths 44, and the catheter assembly (which may include an extension tube), may include an entirety of a blood collection pathway through which blood flows after leaving the vasculature and into or through the blood collection device during blood collection. The system geometric factor $G_{fs}$ for the extended fluid pathway of the blood collection system can be determined in similar fashion as for the fluid pathway (such as the that of the other tube 36 and/or the fluid paths 44) described earlier. In some embodiments, the system geometric factor $G_{fs}$ may be equal to or more than 7.34 E+06 (1/in$^3$) when the translation handle 28 is in the distal position. In some embodiments, $G_{fs}$ may include another value. In some embodiments, the system geometric factor $G_{fs}$ may be 7.34 E+06 (1/in$^3$) plus or minus 10 percent, plus or minus 25 percent, plus or minus 50 percent, or plus or minus 75 percent. In some embodiments, $G_{fs}$ may include another value, which may be selected based on a gauge and/or length of the catheter.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. An extension set, comprising:
   a tube, comprising a distal end, a proximal end, a lumen extending between the distal end and the proximal end, and an outer surface;
   a distal connector coupled to the distal end of the tube;
   a proximal connector coupled to the proximal end of the tube;
   a patency instrument disposed within the tube;
   a translation handle coupled to the outer surface of the tube, wherein the translation handle is configured to move along the outer surface of the tube between a proximal position and a distal position to translate the distal end of the patency instrument between a retracted position and an advanced position, wherein in response to the distal end of the patency instrument being in the advanced position, the distal end of the patency instrument extends beyond the distal end of the tube; and
   a coupler element disposed within the tube, wherein the patency instrument extends distally from the coupler element, wherein the translation handle compresses a portion of the tube in between the coupler element and the translation handle, wherein the portion of the tube engages the coupler element such that movement of the translation handle along the outer surface of the tube translates the coupler element within the tube and the distal end of the patency instrument is moved between the retracted position and the advanced position.

2. The extension set of claim 1, further comprising another tube, wherein the other tube is disposed within the tube and extends through the coupler element, wherein a space between the other tube and the tube is sealed such that fluid is prevented from entering the space, wherein the patency instrument extends through the space.

3. The extension set of claim 2, further comprising a seal adjacent the distal end of the tube, wherein the other tubing and the patency instrument extend through the seal, wherein a distal end of the space is sealed by the seal such that fluid is prevented from entering the space.

4. The extension set of claim 1, wherein the patency instrument comprises a guidewire.

5. The extension set of claim 1, wherein the translation handle comprises a plurality of ball bearings, a plurality of wheels, or a plurality of sliders to provide localized compression of the tube to engage the coupler element.

6. An extension set, comprising
a tube, comprising a distal end, a proximal end, a lumen extending between the distal end and the proximal end, and a circumferential wall that defines the lumen, with the circumferential wall having an outer surface;
a distal connector coupled to the distal end of the tube;
a proximal connector coupled to the proximal end of the tube;
a patency instrument disposed within the tube;
a translation handle coupled to the outer surface of the tube, wherein the translation handle is configured to move along the outer surface of the tube between a proximal position and a distal position to translate the distal end of the patency instrument between a retracted position and an advanced position, wherein in response to the distal end of the patency instrument being in the advanced position, the distal end of the patency instrument extends beyond the distal end of the tube;
a fluid path formed within the circumferential wall of the tube and arranged in parallel to the lumen; and
a coupler element disposed within the tube, wherein the patency instrument extends distally from the coupler element, wherein the translation handle compresses a portion of the tube in between the coupler element and the translation handle, wherein the portion of the tube engages the coupler element such that movement of the translation handle along the outer surface of the tube translates the coupler element within the tube and the distal end of the patency instrument is moved between the retracted position and the advanced position.

7. The extension set of claim 6, wherein the fluid path forms a protrusion into the lumen of the tube, wherein an outer surface of the coupler element comprises a groove aligned with the protrusion, wherein the groove extends through the coupler element.

8. The extension set of claim 6, wherein the lumen is sealed from the fluid path.

9. The extension set of claim 8, further comprising a seal disposed adjacent the distal end of the tube, wherein the seal comprises a hole aligned with the fluid path, wherein the patency instrument extends through the seal, wherein the lumen is sealed from the fluid path by the seal.

10. The extension set of claim 6, wherein the patency instrument comprises a guidewire.

11. The extension set of claim 6, wherein the translation handle comprises a plurality of ball bearings or a plurality of wheels to provide localized compression of the tube to engage the coupler element.

12. The extension set of claim 6, wherein the extension set comprises a plurality of fluid paths disposed within the wall of the tube.

13. The extension set of claim 6, wherein the circumferential wall of the tube has a thickness, and wherein the fluid path is formed within the thickness of the wall, with a diameter that is less than the thickness of the wall.

* * * * *